United States Patent [19]

Robins et al.

[11] Patent Number: 4,760,137
[45] Date of Patent: Jul. 26, 1988

[54] METHOD FOR THE PRODUCTION OF 2'-DEOXYADENOSINE COMPOUNDS

[75] Inventors: Roland K. Robins, Provo; Ganapathi R. Revankar, Orem, both of Utah

[73] Assignee: Brigham Young University, Provo, Utah

[21] Appl. No.: 8,048

[22] Filed: Jan. 15, 1987

Related U.S. Application Data

[63] Continuation of Ser. No. 638,192, Aug. 6, 1984, abandoned.

[51] Int. Cl.$^4$ ............................................. C07H 19/173
[52] U.S. Cl. ........................................... 536/26; 536/24
[58] Field of Search .................................... 536/24, 26

[56] References Cited

U.S. PATENT DOCUMENTS 3,225,029 12/1965 Yamaoka ............................. 536/24
3,314,938 4/1967 Kawashima et al. ................ 536/24
3,708,469 1/1973 Vorbruggen et al. ............... 536/23

OTHER PUBLICATIONS

1Z. Kazimierczuk et al., "Total Synthesis of Certain 2-6-Mono- and 2,6-Disubstituted-Tubercidin Derivatives. Synthesis of Tubercidin Via the Sodium Salt Glycosylation Procedure", Feb. 1984, pp. 1179–1184.
Kazimierczuk et al., Synthesis of-2'-Deoxyadenosine and Related 2'-Deoxynucleosides Via a Novel Sodium Salt Glycosylation Procedure, J. Am. Chem. Soc. 106, 6379, (1984).
Katz et al., Synthesis of Pyridazine Analogs of-Nucleosides ..., J. Med. Chem. 25, 813, (1982).
Showalter et al., Studies Related to the Total Synthesis of Pentostatin ..., Tetrahedron Letters 22 (33), 3155, (181).
Robins et al., Purine Deoxynucleosides, Synthesis ... by the Fusion Method, J. Am. Chem. Soc. 86, 1251, (1964).
Skulnick et al., A New Synthesis of . . . Dihydro-5-Azathymidine ..., Chem. Abstracts 92:42320j, (1980).
Ullman et al., Deoxyadenosine ... Cytotoxicity in Cultured Mouse T–Lymphoma Cells..., Chem. Abstracts 92:178816h, (1980).
Saneyoshi et al., Synthetic Nucleosides ... Ribosylation of Several 6-Substituted Purines, Chem. Abstracts 92:147100r, (1979).
Wierenga et al., Stereochemical Control ... in 2-Deoxy-D-Erythro-Pentofuranosyl Nucleosides, Carbohydrate Research 90, 41, (1981).

*Primary Examiner*—J. R. Brown
*Assistant Examiner*—Elli Peselev
*Attorney, Agent, or Firm*—Krass and Young

[57] ABSTRACT

A method that is direct and stereospecific is provided for the production of 2'-deoxyadenosine derivatives and related analogs. The method comprises glycosylation of the sodium salt of 2,6-dichloropurine or 6-chloropurine and ammonolysis of the glycosylate to obtain the corresponding 2-chloro-2'-deoxyadenosine or 2'-deoxyadenosine.

9 Claims, No Drawings

METHOD FOR THE PRODUCTION OF 2'-DEOXYADENOSINE COMPOUNDS

This is a continuation of co-pending application Ser. No. 638,192 filed on Aug. 6, 1984, now abandoned.

TECHNICAL FIELD

This invention relates to a method for the production of 2'-deoxyadenosine compounds and related analogs, comprising a direct stereospecific glycosylation of a purine aglycon.

BACKGROUND OF THE INVENTION

Prior glycosylation procedures in which the 2-deoxy-β-D-ribofuranosyl (2-deoxy-β-D-erythro-pentofuranosyl) moiety is introduced into an aglycon invariably provide anomeric mixtures as well as positional isomers which result in very low yields of the desired 2'-deoxynucleoside. In view of these difficulties, a four-step deoxygenation procedure using phenoxythiocarbonylation (J.A.C.S. 1983, 105, 4059) or imidazolylthiocarbonylation (J. Org. Chem. 1982, 47, 485; Chem. Pharm. Bull. 1983, 31, 1842) of the 2'-hydroxy group of the corresponding 3',5'-protected β-D-ribonucleoside has been developed to provide the requisite 2'-deoxynucleoside. What the art lacks, however, are improved procedures that do not require the availability of the preformed ribonucleoside and also are applicable in the presence of haloheterocylic derivatives, which are the most useful for further nucleophilic displacement.

SUMMARY AND DETAILED DESCRIPTION

The present invention, which overcomes the difficulties and shortcomings of the prior art, concerns a method of producing 2'-deoxyadenosine compounds, comprising glycosylating a sodium salt of a purine compound having the formula

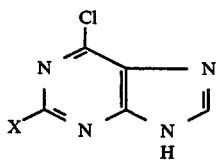

with 1-chloro-2-deoxy-3,5-di-O-p-toluoyl-α-D-erythropentofuranose, isolating the resulting 9-(2-deoxy-3,5-di-O-p-toluoyl-β-D-erythro-pentofuranosyl) purine having the formula I

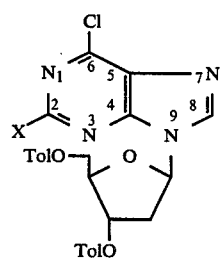

and subjecting the same to ammonolysis under deblocking conditions to obtain the corresponding 2'-deoxyadenosine having the formula II

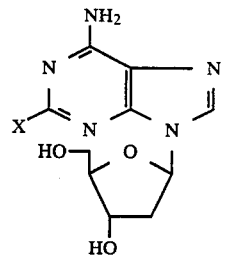

where X is hydrogen or Cl.

The glycosylation step of the method is carried out in a polar solvent, preferably acetonitrile, at ambient temperature. The sodium salt of the purine compound preferably is formed in situ by reaction of the purine compound and sodium hydride. The reaction is usually complete within 0.5 hour. The glycosylation is carried out at ambient temperature until complete, usually within about 15 hours. The specificity of the glycosylation step and the high yield produced of the desired 6-chloro-9-glycosylated product were both unexpected. Although a polar solvent was used, which would tend to favor sugar anomerization and thus resulting in approximately equal amounts of the alpha and beta nucleosidic products, the desired β-glycosylation was rapid and preferentially took place without appreciable anomerization. Since the starting 1-chloro-2-deoxy-3,5-di-O-p-toluoyl-D-erythropentofuranose has the α-configuration in the solid state, the exclusive formation of the blocked 2'-deoxy-β-nucleosides is viewed to be due to a direct Walden inversion ($S_N2$) at the $C_1$ carbon by the anionic heterocyclic nitrogen. Inasmuch as the reaction mixture may contain a minor amount of positional isomers, the product is isolated from the reaction mixture in any suitable way, preferably by recrystallization. The ammonolysis is conveniently carried out by heating a solution of the 6-chloro-9-pentofuranosylpurine product in methanolic ammonia at elevated temperature, preferably about 100° C., until the reaction is complete, usually for a period of from about 5 to about 12 hours. The products of the method, 2'-deoxyadenosine and 2-chloro-2'-deoxyadenosine, are useful cytotoxic agents and are useful as intermediates for the production of 2'-deoxyadenosine analogs (Cf. Proc. Am. Assoc. Cancer Res. 1980, 72, 302; Cancer Res. 1982, 42, 3911).

The invention is illustrated, and the best mode of carrying out the same is set forth, in the following examples.

GENERAL PROCEDURES

Melting points were taken on a Thomas-Hoover capillary melting point apparatus and are uncorrected. Nuclear magnetic resonance ($^1$H NMR) spectra were determined at 90 MHz with a JEOL FX 900 spectrometer. The chemical-shift values are expressed in delta values (parts per million) relative to tetramethylsilane as an internal standard. Ultraviolet spectra (UV; sh=shoulder) were recorded on a Cary Model 15 spectrophotometer. Evaporations were carried out under reduced pressure with the bath temperature below 30° C.

EXAMPLE 1

2,6-Dichloro-9-(2-deoxy-3,5-di-O-p-toluoyl-β-D-erythro-pentofuranosyl)-purine a. A mixture of 2,6-dichloropurine (0.95 g, 5 mmol) and sodium hydride (50% in oil, 0.25 g, 5.2 mmol) in anhydrous $CH_3CN$ (35 mL) was stirred at ambient temperature under a nitrogen atmosphere for 30 min. Dry, powdered 1-chloro-2-deoxy-3,5-di-O-p-toluoyl-α-D-erythro-pentofuranose (1.95 g, 5 mmol) was added portionwise with stirring, during 20 min, and stirring was continued for a further 15 h. Evaporation of the solvent gave an oily residue, which was purified on a silica gel column (5×60 cm) using toluene:acetone (9:1, v/v) as the solvent. Two nucleosides were isolated in the order listed: the title compound was crystallized from EtOH to yield 1.60 g (59%); mp 159°–162° C. [Literature mp 155°–157° C.].

b. The N-7 glycosyl isomer 2,6-dichloro-7-(2-deoxy-3,5,di-O-p-toluoyl-β-D-erythro-pentofuranosyl)-purine was isolated and crystallized from EtOH to yield 0.35 g (13%); mp 141°–143° C. $^1H$ NMR ($Me_2SO$-$d_6$) δ6.88 (t, 1, $C_1$, $\underline{H}$, peak width 14.5 Hz), 7.36 and 7.90 (m, 8, Ph), 9.28 (s, 1, $C_8\underline{H}$). Anal. Calcd for $C_{26}H_{22}Cl_2N_4O_5$ (541.4): C, 57.68; H, 4.09; N, 10.35. Found: C, 57.55; H, 4.00; N, 10.36.

2-Chloro-6-amino-9-(2-deoxy-β-D-erythropentofuranosyl)purine (2-Chloro-2′-deoxyadenosine)

c. A solution of the 2,6-dichloro-9-pentofuranosylpurine product of 1a) (2.50 g, 4.6 mmol) in $CH_3OH/NH_3$ (saturated at 0° C., 60 ml) was heated at 100° C. for 5 h and the mixture was evaporated to dryness. The residue was purified on a silica gel column (5×40 cm) using $CHCl_3$:MeOH (8:2, v/v) as the solvent. Crystallization of the homogeneous solid from EtOH gave 0.87 g (71%) of analytically pure title compound; mp 220° C. (softens), resolidifies, turns brown, does not melt below 300° C. [Lit. mp 210°–215° C. (softens) and then solidifies and turns brown].

EXAMPLE 2

6-Chloro-9-(2-deoxy-3,5-di-O-p-toluoyl-β-D-erythropentofuranosyl)purine a. In the same manner as for Example 1, reaction of the sodium salt of 6-chloropurine (0.77 g, 5 mmol and 50% NaH in oil, 0.25 g, 5.2 mmol) with 1-chloro-2-deoxy-3,5-di-O-p-toluoyl-α-D-erythro-pentofuranose (2.0 g, 5.15 mmol) in $CH_3CN$ (50 mL) gave 1.51 g (59%) of crystalline title compound (from EtOH); mp 107°–109° C. $^1H$ NMR ($Me_2SO$-$d_6$) δ6.76 (t, 1, $C_1$, $\underline{H}$, peak width 14.0 Hz), 7.36 and 7.94 (m, 8, Ph), 8.80 (s, $\overline{1}$, $C_2H$), 9.00 (s, 1, $C_1\underline{H}$). Anal. Calcd for $C_{26}H_{23}ClN_4O_5$ (506.9): C, 61.60; H, 4.57; N, 11.05. Found: C, 61.73; H, 4.72; N, 11.03.

b. The N-7 glycosyl isomer 6-chloro-7-(2-deoxy-3,5-di-O-p-toluoyl-β-D-erythropentofuranosyl)purine was isolated and crystallized from EtOH to yield 0.29 g (11%); mp 152°–153° C. $^1H$ NMR ($Me_2SO$-$d_6$) δ6.96 (t, 1, $C_1$, $\underline{H}$, peak width 14.5 Hz), 7.36 and 7.94 (m, 8, Ph), 8.94 (s, $\overline{1}$, $C_2\underline{H}$), 9.26 (s, 1, $C_8\underline{H}$).

Anal. Calcd for $C_{26}H_{23}ClN_4O_5$ (506.9): C, 61.60; H, 4.57; N, 11.05. Found: C, 61.55; H, 4.49; N, 11.05. cl 6-Amino-9-(2-deoxy-β-D-erythro-pentofuranosyl)purine (2′-Deoxyadenosine)

c. A solution of the 6-chloro-9-pentofuranosylpurine product of 2a) (1.01 g, 2 mmol) in $MeOH/NH_3$ (18 mL) was heated at 100° C. for 12 h and then evaporated to dryness. The aqueous solution of the residue was extracted with $CHCl_3$ (2×25 mL), followed by ether (2×25 mL) and then evaporated to dryness. The residue was crystallized from water to yield 0.41 g (78%); mp 186°–189° C. [Lit. mp 187°–189° C., and all other physicochemical properties of the title 2′-deoxyadenosine product are identical with 2′-deoxyadenosine reported in the literature].

The embodiments of the invention in which an exclusive property or privilege is claimed are defined as follows:

1. A method of producing 2′-deoxyadenosine compounds, comprising the direct stereospecific step of glycosylating the sodium salt of a purine compound having the formula

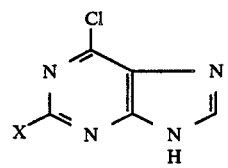

with 1-chloro-2-deoxy-3,5-di-O-p-toluoyl-α-D-erythropentofuranose in acetonitrile employed as a solvent at ambient temperature, thereby obtaining a reaction mixture in which glycosylated purines are formed exclusively without appreciable anomerization and are the beta glycosylated purines 7- and 9-(2-deoxy-3,5-di-O-p-toluoyl-β-D-erythro-pentofuranosyl)purines and the further steps of isolating the resulting 9-(2-deoxy-3,5-di-O-p-toluoyl-β-D-erythro-pentofuranosyl)purine having the formula I

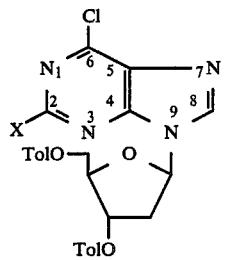

subjecting the same to ammonolysis under deblocking conditions to obtain the corresponding 2′-deoxyadenosine product having the formula II

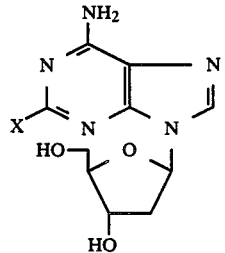

where X is hydrogen or Cl, and isolating the 2′-deoxyadenosine product.

2. A method according to claim 1 where the sodium salt is formed in situ at ambient temperature by reaction of the purine compound and sodium hydride.

3. A method according to claim 1 where the ammonolysis is carried out by heating a solution of the 6-chloro-9-pentofuranosylpurine product in methanolic ammonia at elevated temperature.

4. A method according to claim 1 where the purine compound is 2,6-dichloropurine.

5. A method according to claim 1 where the purine compound is 6-chloropurine.

6. 2,6-Dichloro-9-(2-deoxy-3,5-di-O-p-toluoyl-β-D-erythro-pentofuranosyl)purine.

7. 6-Chloro-9-(2-deoxy-3,5-di-O-p-toluoyl-β-D-erythro-pentofuranosyl)purine.

8. 2-Chloro-2'-deoxyadenosine produced from the 2,6-dichloro-9-(2-deoxy-3,5-di-O-p-toluoyl-B-D-erythro=pentofuranosyl)purine isomer by the method according to claim 1.

9. 2'-Deoxyadenosine produced from the 6-chloro-9-(2-deoxy-3,5-di-O-p-toluoyl-B-D-erythro pentofuranosyl)purine isomer by the method according to claim 1.

* * * * *

UNITED STATES PATENT AND TRADEMARK OFFICE
CERTIFICATE OF CORRECTION

PATENT NO. : 4,760,137
DATED : July 26, 1988
INVENTOR(S) : Robins et al

It is certified that error appears in the above-identified patent and that said Letters Patent is hereby corrected as shown below:

Column 2, line 51, "72" should be --71--.

Signed and Sealed this

Thirteenth Day of December, 1988

Attest:

DONALD J. QUIGG

*Attesting Officer*      *Commissioner of Patents and Trademarks*